(12) United States Patent
Umezawa

(10) Patent No.: US 11,955,226 B2
(45) Date of Patent: Apr. 9, 2024

(54) INFORMATION PROCESSING APPARATUS, TOMOGRAPHIC APPARATUS, AND INFORMATION PROCESSING METHOD

(71) Applicants: CANON KABUSHIKI KAISHA, Tokyo (JP); CANON MEDICAL SYSTEMS CORPORATION, Tochigi (JP)

(72) Inventor: Kohtaro Umezawa, Tokyo (JP)

(73) Assignees: CANON KABUSHIKI KAISHA, Tokyo (JP); CANON MEDICAL SYSTEMS CORPORATION, Tochigi (JP)

(*) Notice: Subject to any disclaimer, the term of this patent is extended or adjusted under 35 U.S.C. 154(b) by 498 days.

(21) Appl. No.: 17/007,548

(22) Filed: Aug. 31, 2020

(65) Prior Publication Data
US 2021/0065880 A1  Mar. 4, 2021

(30) Foreign Application Priority Data
Aug. 30, 2019 (JP) .................... 2019-158315

(51) Int. Cl.
| | |
|---|---|
| G06K 9/00 | (2022.01) |
| G06N 5/04 | (2023.01) |
| G06T 7/00 | (2017.01) |
| G16H 30/20 | (2018.01) |

(52) U.S. Cl.
CPC ............. *G16H 30/20* (2018.01); *G06N 5/04* (2013.01); *G06T 7/0014* (2013.01); *G06T 2207/10072* (2013.01)

(58) Field of Classification Search
CPC . G06T 2207/10072; G06T 2207/10081; G06T 2207/20084; G06T 2207/30101; G06T 2207/30168; G06T 7/0002; G06T 7/0014; G16H 30/20; G16H 30/40; G16H 50/20
See application file for complete search history.

(56) References Cited

U.S. PATENT DOCUMENTS

| | | | |
|---|---|---|---|
| 6,173,068 B1 | 1/2001 | Prokoski | |
| 9,384,326 B2 | 7/2016 | Kawagishi et al. | |
| 10,282,838 B2 | 5/2019 | Nunes et al. | |
| 10,799,189 B2 * | 10/2020 | Nye | A61B 6/032 |
| 11,165,997 B2 * | 11/2021 | Ishii | H04N 9/317 |
| 11,227,389 B2 | 1/2022 | Song et al. | |
| 11,424,033 B2 | 8/2022 | Kawagishi et al. | |
| 11,769,254 B2 | 9/2023 | Song et al. | |

(Continued)

FOREIGN PATENT DOCUMENTS

| | | |
|---|---|---|
| CN | 102385664 A | 3/2012 |
| CN | 108324297 A | 7/2018 |

(Continued)

*Primary Examiner* — Avinash Yentrapati
(74) *Attorney, Agent, or Firm* — VENABLE LLP

(57) ABSTRACT

An information processing apparatus includes a processor, and a memory storing a program. The program, when executed by the processor, causes the information processing apparatus to: acquire a medical image obtained by imaging a subject, acquire an inspection result of the medical image, perform inference on the medical image; and control outputting of an inference result of the medical image inference to an external device based on the inspection result of the medical image.

12 Claims, 6 Drawing Sheets

(56) References Cited

U.S. PATENT DOCUMENTS

| | | | |
|---|---|---|---|
| 2008/0219530 A1* | 9/2008 | Levanon | A61B 5/02007 |
| | | | 702/19 |
| 2011/0110572 A1* | 5/2011 | Guehring | A61B 6/5258 |
| | | | 382/128 |
| 2012/0054652 A1 | 3/2012 | Kawagishi et al. | |
| 2016/0128648 A1* | 5/2016 | Miyazawa | A61B 6/466 |
| | | | 378/21 |
| 2017/0004351 A1* | 1/2017 | Kim | G06V 40/1365 |
| 2018/0197288 A1 | 7/2018 | Nunes et al. | |
| 2019/0150857 A1* | 5/2019 | Nye | G16H 30/40 |
| 2019/0156942 A1* | 5/2019 | Pronk | G16H 40/63 |
| 2019/0164285 A1* | 5/2019 | Nye | G16H 10/60 |
| 2019/0205515 A1* | 7/2019 | Lee | G06F 21/32 |
| 2019/0261938 A1* | 8/2019 | Sevenster | G06F 18/00 |
| 2020/0005942 A1 | 1/2020 | Kawagishi et al. | |
| 2020/0288066 A1* | 9/2020 | Candelore | H04N 23/64 |
| 2020/0402237 A1 | 12/2020 | Song et al. | |
| 2021/0015433 A1 | 1/2021 | Nye et al. | |
| 2022/0001210 A1* | 1/2022 | Letourneau | G16H 30/20 |
| 2022/0067935 A1 | 3/2022 | Song et al. | |
| 2022/0207722 A1* | 6/2022 | Kim | G06T 7/11 |

FOREIGN PATENT DOCUMENTS

| | | | |
|---|---|---|---|
| CN | 109378043 A | 2/2019 | |
| JP | 2015-150062 A | 8/2015 | |
| JP | 2018-166961 A | 11/2018 | |
| JP | 2019-93137 A | 6/2019 | |

\* cited by examiner

INFORMATION PROCESSING APPARATUS, TOMOGRAPHIC APPARATUS, AND INFORMATION PROCESSING METHOD

BACKGROUND OF THE INVENTION

Field of the Invention

The present invention relates to an information processing apparatus that process a medical image, a tomographic apparatus, an information processing method, and a program.

Description of the Related Art

In the medical field, medical images are captured by various modality apparatuses. A computed tomography (CT) apparatus, an X-ray diagnostic apparatus, a magnetic resonance imaging (MRI) apparatus, and an ultrasonic diagnostic apparatus can be used as the modality apparatuses. And a check is performed to determine whether medical images are appropriately captured. The checking operation is referred to as, for example, inspection.

The inspected medical images are transmitted to a picture archiving and communication system (PACS) that stores and manages medical images.

The inspection is performed by, for example, a computer in some cases. Japanese Patent Application Publication No. 2015-150062 discloses a technology for supplying a warning based on quality or the like of medical images subjected to image processing when the medical images captured by a modality apparatus are subjected to image processing.

An operation called inference is performed on medical images, for example, to detect lesions or determine whether there are abnormal parts or determine whether target parts are normal. However, there is a possibility of inference not being correctly performed when the inference is not performed based on medical images acceptable for inspection.

The technology of the present disclosure has been devised in view of the foregoing circumstances and an objective of the present disclosure is to perform inference on a medical image based on an appropriate inspection result.

SUMMARY OF THE INVENTION

In order to achieve the above objective, it is provided an information processing apparatus including a processor, and a memory storing a program which, when executed by the processor, causes the information processing apparatus to: acquire a medical image obtained by imaging a subject, a second acquisition unit configured to acquire an inspection result of the medical image, perform inference on the medical image, and control outputting of an inference result of the medical image by the inference to an external device based on an inspection result of the medical image.

And, in order to achieve the above objective, it is provided an information processing apparatus including a processor, and a memory storing a program which, when executed by the processor, causes the information processing apparatus to: acquire a medical image obtained by imaging a subject, acquire an inspection result of the medical image, perform inference on the medical image, and control performing inference on the medical image based on the inspection result of the medical image.

Further, in order to achieve the above objective, it is provided an information processing method including the steps of acquiring, by a first acquisition mechanism, a medical image obtained by imaging a subject, acquiring, by a second acquisition mechanism, an inspection result of the medical image, performing, by an inference mechanism, inference on the medical image, and controlling, by a control mechanism, outputting of an inference result of the medical image by the inference mechanism to an external device based on an inspection result of the medical image acquired by the second acquisition mechanism.

And, in order to achieve the above objective, it is provided an information processing method including the steps of acquiring, by a first acquisition mechanism, a medical image obtained by imaging a subject, acquiring, by a second acquisition mechanism, an inspection result of the medical image, performing, by an inference mechanism, inference on the medical image, and controlling, by a control mechanism, performing inference on the medical image by the inference mechanism based on an inspection result of the medical image acquired by the second acquisition mechanism.

And, in order to achieve the above objective, it is provided a non-transitory computer-readable storage medium that stores a program causing a computer to execute the information processing method as described above.

And, in order to achieve the above objective, it is provided a tomographic apparatus including the information processing apparatus as described above, and a data collection unit configured to collect tomographic data of the subject, wherein the program further causes the information processing apparatus to acquire the medical image based on the tomographic data.

Further features of the present invention will become apparent from the following description of exemplary embodiments with reference to the attached drawings.

DESCRIPTION OF THE EMBODIMENTS

Hereinafter, preferred embodiments of the technology according to the present disclosure will be described with reference to the drawings. Here, dimensions, materials, shapes, relative dispositions, and the like of constituent components to be described below are appropriately changed depending on various conditions or configurations of apparatuses to which the present invention is applied. Accordingly, the scope of the present invention is not limited to the following description. In particular, general or known technologies of the technology fields can be applied to configurations or processes which are not illustrated or described. Repeated description will be omitted in some cases.

First Embodiment

Figure 1:
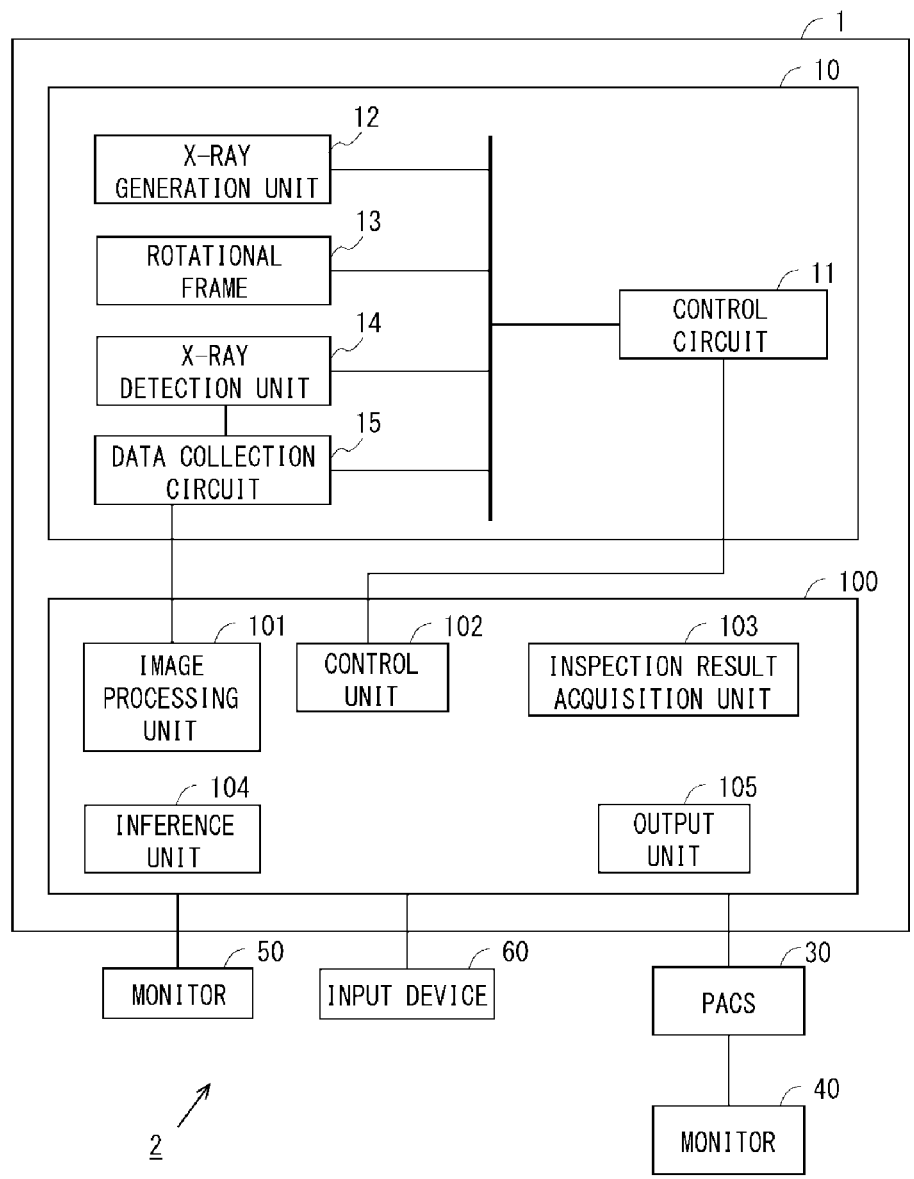
FIG. 1 is a functional block diagram illustrating an information processing system according to a first embodiment.

First, an example of a problem solved by an information processing apparatus according to a first embodiment will be described. FIG. 1 is a functional block diagram illustrating an information processing system 2 including a tomographic apparatus 1, a PACS 30, monitors 40 and 50, and an input device 60 according to the embodiment. The tomographic device 1 includes a gantry 10 and a console 100.

For example, the gantry 10 is installed in a CT examination room and the console 100 is installed in a control room adjacent to the CT examination room. The gantry 10 and the console 100 are connected to be able to communicate with each other.

An imaging mechanism for X-ray CT imaging is mounted on the gantry 10. The console 100 is a computer that controls the gantry 10. The console 100 is connected to the PACS 30, the monitor 50, and the input device 60. A user (an operator or the like) of the console 100 operates the input device 60 to give various instructions to the console 100 and checks processing results of the console 100 on the monitor 50. The PACS 30 is connected to the monitor 40. A doctor or the like displays medical images managed by the PACS 30 on the monitor 40 to perform interpretation of the images. Any connection form of each device can be used in addition to wired connection and wireless connection. The PACS 30 and the monitors 40 and 50 are examples of an external device.

As illustrated in FIG. 1, the gantry 10 includes a control circuit 11, an X-ray generation unit 12, a rotational frame 13, an X-ray detection unit 14, and a data collection circuit 15. The gantry 10 is an example of a data collection unit that collects tomographic data of a subject. The control circuit 11 controls driving of the X-ray generation unit 12, the rotational frame 13, the X-ray detection unit 14, and the data collection circuit 15. The X-ray generation unit 12 shapes X rays generated in an X-ray tube using a collimator and radiates the shaped X rays toward the rotational frame 13. The rotational frame 13 is a substantially cylindrical metal frame that has an opening and is supported to be rotatable in the gantry 10. In the opening of the rotational frame 13, a bed is provided and a subject is placed on the bed.

The X-ray detection unit 14 causes a detection element to detect the X rays radiated from the X-ray generation unit 12 to the subject placed on the bed of the rotational frame 13. The detection element includes a scintillator and an optical sensor. In the detection element, the scintillator converts the X rays incident on the detection element into light with a photon amount in accordance with an incident X-ray amount and the optical sensor amplifies the light to convert the light into an electrical signal. The data collection circuit 15 generates tomographic data of the subject having a digital value in accordance with a dose of the X rays by reading and amplifying the electrical signal in accordance with the dose of the X rays detected by the X-ray detection unit 14 and integrating the amplified electrical signal for a view period.

Figure 2:
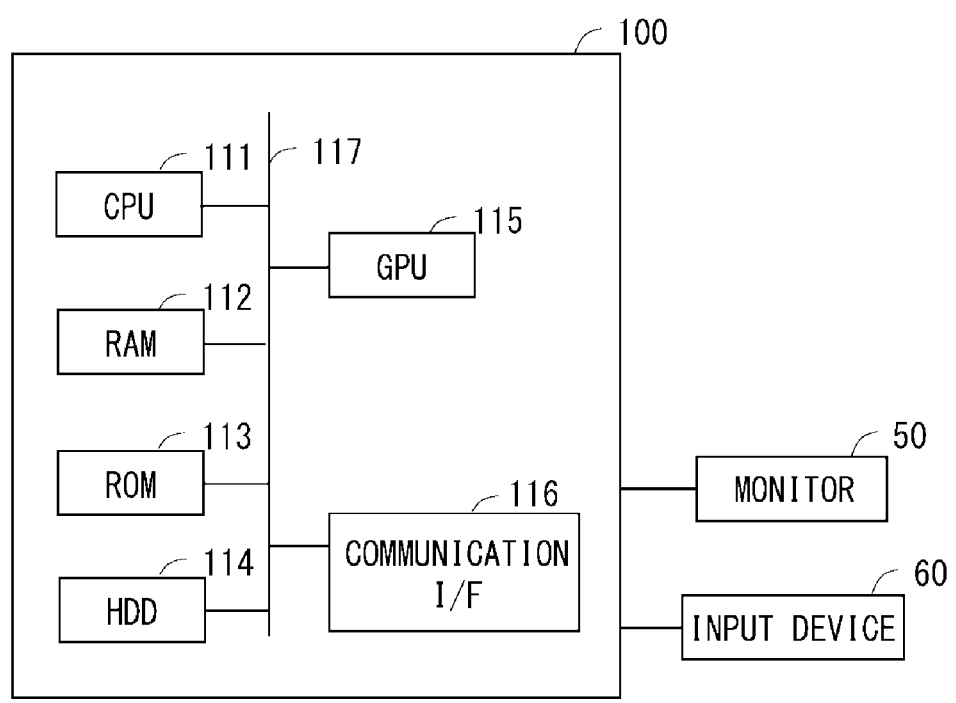
FIG. 2 is a schematic diagram illustrating a configuration of an information processing apparatus according to the first embodiment.

FIG. 2 is a schematic diagram illustrating a hardware configuration of the console 100. The console 100 includes a central processing unit (CPU) 111. The console 100 includes a random access memory (RAM) 112, a read only memory (ROM) 113, and a hard disk drive (HDD) 114. Further, the console 100 includes a graphics processing unit (GPU) 115 and a communication interface (I/F) 116. The CPU 111, the RAM 112, the ROM 113, the HDD 114, the GPU 115, and the communication I/F 116 are connected to each other via a system bus 117. In the embodiment, the CPU 111 loads and executes various programs stored in the HDD 114 on the RAM 112 to function as an image processing unit 101, a control unit 102, an inspection result acquisition unit 103, an inference unit 104, and an output unit 105 illustrated in FIG. 1.

The configurations of the console 100 may be configured as separate devices or may be configured as a single integrated device. The console 100 may be configured as a single device in which at least some of the configurations of the console 100 are integrated.

Image Processing Unit 101

The image processing unit 101 receives the tomographic data generated from the data collection circuit 15 of the gantry 10 and performs preprocessing such as logarithmic conversion or correction processing on the tomographic data to generate CT images of the subject based on the processed data. The CT image is an example of a medical image. The image processing unit 101 is an example of a first acquisition unit and a first acquisition mechanism acquiring medical images of the subject. In the embodiment, information regarding a subject related to imaging or an imaging order included in check factors are provided in advance and the operator of the tomographic apparatus 1 images the subject based on the imaging order. The tomographic data collected by the data collection circuit 15 may be transmitted automatically to the console 100. Alternatively, an operator or the like who is the user of the console 100 may operate a graphical user interface (GUI) (not illustrated) displayed on the monitor 50 to designate CT images. In this case, the image processing unit 101 acquires the tomographic data to be used to generate the designated CT images from the data collection circuit 15.

Inspection Result Acquisition Unit 103

The inspection result acquisition unit 103 acquires an inspection result for checking whether a medical image acquired by the image processing unit 101 is appropriately captured. The inspection is processing of checking whether images are appropriately captured by a modality apparatus. The inspection includes, for example, processing of checking whether the medical images include false images, whether halation caused due to artifacts occurs in the medical images, or whether an imaging target image included in the medical images is distorted. The inspection also includes processing of checking whether the medical images satisfy accuracy required in the processing of inference as described later. Further, the inspection may include, for example, processing of checking whether the medical images have resolutions appropriate for diagnosis, whether the disposition of the medical images is appropriate for diagnosis, and whether a region of interest in a subject is imaged. In the following description, a case in which a medical image is appropriately captured as a result of inspection is referred to as an acceptable result. A case in which a medical image is not appropriately captured is referred to as an unacceptable result. The inspection result acquisition unit 103 is an example of a second acquisition unit and a second acquisition mechanism acquiring an inspection result of a medical image of the subject.

In the embodiment, the operator or the like operates the input device 60 to inspect the medical image. The operator or the like operates the input device 60 to display the medical image acquired by the image processing unit 101 on the monitor 50. Then, the operator or the like operates a GUI or the like displayed on the monitor 50 to check the medical image and presses an acceptable button (not illustrated) displayed on the monitor 50 when the medical image is acceptable. When the medical image is unaccepted, the operator or the like presses an unacceptable button (a failure button) (not illustrated) displayed on the monitor 50. The operator or the like presses a re-scan button to make a re-scan request. The operator or the like can also operate a GUI or the like displayed on the monitor 50 to input a comment regarding the inspection of the medical image. For example, when the operator or the like determines that the inspection of the medical image is unacceptable, the operator or the like operates a GUI or the like displayed on the monitor 50 to input the reason why the inspection is unacceptable. The inspection result acquisition unit 103 acquires the acceptable or unacceptable result or the comment on the medical image displayed on the monitor 50 by the operator or the like as an inspection result. The input device 60 may include an acceptable button, an unacceptable button (a failure button) or a re-scan button.

Inference Unit 104

The inference unit 104 performs inference on the medical image acquired by the image processing unit 101. In the embodiment, a learned model in which a medical image including a part of aortic dissection is learned as a target is generated in advance by machine learning using a known deep network such as a convolutional neural network (CNN). The inference unit 104 performs inference on the medical image using the generated model to detect a region of the aortic dissection in a medical image or draw a local region. The inference content is not limited thereto and a probability or the like of the aortic dissection being included in the local region in the medical image may be calculated by the inference, or a probability or the like of the aortic dissection being included in the medical image may be calculated. The inference unit 104 may perform inference using a calculation expression or the like for calculating a probability of aortic dissection occurring instead of or in addition to the use of the model. The inference unit 104 is an example of an inference mechanism performing inference on a medical image.

Output Unit 105

The output unit 105 outputs the medical image, the inspection result, and the inference result acquired on the console 100 to the PACS 30, the monitor 50, and the like based on an instruction from the control unit 102.

Control Unit 102

The control unit 102 controls each unit in the console 100. The control unit 102 controls imaging of the subject on the gantry 10 by controlling the control circuit 11 of the gantry 10. The control unit 102 controls the inference on the medical image by the inference unit 104 based on the inspection result acquired by the inspection result acquisition unit 103. Here, the control of the inference of the inference unit 104 by the control unit 102 means that the control unit 102 gives the inference unit 104 various instructions to perform the inference. For example, the control unit 102 instructs the inference unit 104 to perform inference on the medical image of which the inspection result acquired by the inspection result acquisition unit 103 is acceptable. On the other hand, the control unit 102 instructs the inference unit 104 not to perform inference on a medical image of which the inspection result acquired by the inspection result acquisition unit 103 is unacceptable. In a case in which the inspection result acquired by the inspection result acquisition unit 103 is unacceptable, the control unit 102 instructs the inference unit 104 to stop the inference when the inference unit 104 is performing the inference on the medical image of which the inspection result is unacceptable. When the inference unit 104 stops the inference on a given medical image, the inference unit 104 proceeds to the inference on a subsequent medical image.

In the embodiment, the control unit 102 may output the medical image, the inspection result, and the inference result from the output unit 105 to an HDD to be described below in the console 100. When the inspection result acquired by the inspection result acquisition unit 103 is unacceptable, the control unit 102 may cause a speaker, a lamp, or the like (not illustrated) to output a sound or light from the output unit 105 to inform the operator or the like of the inspection result. Alternatively or in addition, when the inspection result acquired by the inspection result acquisition unit 103 is acceptable, the control unit 102 may cause a speaker, a lamp, or the like to output a sound or light from the output unit 105 to inform the operator or the like of the inspection result. The methods of informing of the inspection result by output unit 105 in the unacceptable and acceptable cases of the inspection result can each be set appropriately. Further, when the control unit 102 instructs the inference unit 104 to stop the inference from the output unit 105, the control unit 102 may inform the operator or the like of the stop of the inference.

The control unit 102 may output a message for requesting re-scan of the medical image of which the inspection result is unacceptable from the output unit 105 to the monitor 50 to prompt the operator or the like to perform re-scan of the medical image. When the inspection result is acceptable, the control unit 102 may output a message indicating that the inspection result is acceptable or a message indicating that the inference result is output from the output unit 105 to the monitor 50. Conversely, when the inspection result acquired by the inspection result acquisition unit 103 is unacceptable, the control unit 102 may be configured to control the control circuit 11 such that the subject on the gantry 10 is automatically re-scanned. Further, the control unit 102 may be configured to stop the inference by the inference unit 104 when the subject is re-scanned. The control unit 102 may be configured not to stop the inference by the inference unit 104 when the subject is not re-scanned.

In the embodiment, the image processing unit 101, the control unit 102, the inspection result acquisition unit 103, the inference unit 104, and the output unit 105 are realized as applications which can be executed in the console 100. Here, such processing units of the console 100 may be realized as an on-premise system. Alternatively, the image processing unit 101, the control unit 102, the inspection result acquisition unit 103, the inference unit 104, and the output unit 105 may be realized as programs on a cloud or a network such as a server to be executed.

Processing Flow

Figure 3:
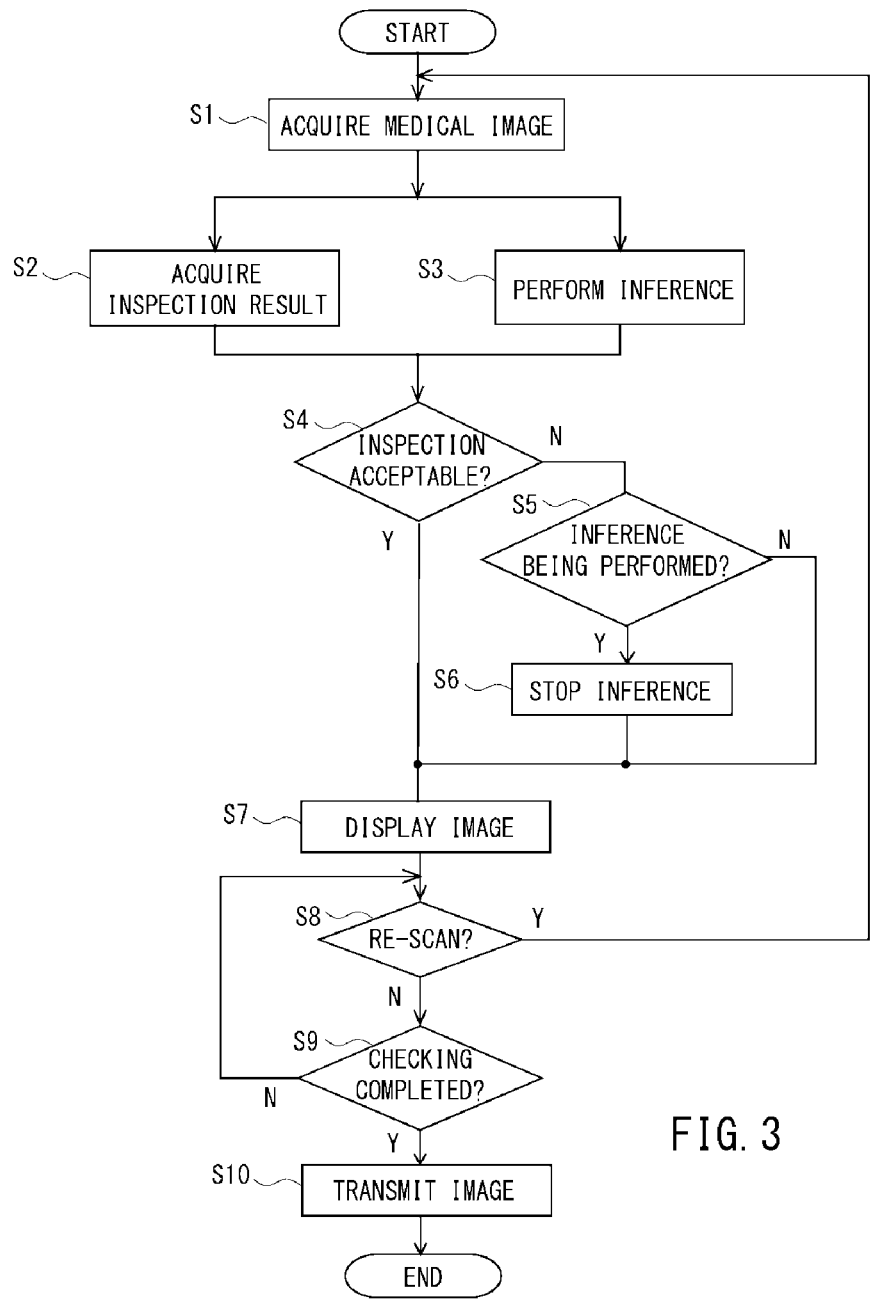
FIG. 3 is a flowchart illustrating processing performed according to the first embodiment.

Next, processing performed by the CPU 111 of the console 100 according to the embodiment will be described with reference to the flowchart of FIG. 3. In the embodiment, the CPU 111 controls inference on a medical image based on an inspection result of the medical image of a subject imaged on the gantry 10.

In step S1, the CPU 111 generates the medical image of the subject based on data received from the data collection circuit 15 of the gantry 10. Thus, the CPU 111 acquires the medical image of the subject. Subsequently, in step S2, the CPU 111 displays the medical image acquired in step S on the monitor 50 in response to an operation of the input device 60 by the operator or the like. The operator or the like inspects the medical image displayed on the monitor 50. Then, the operator or the like uses the acceptable button or the unacceptable button displayed on the monitor 50 to determine whether the medical image is acceptable or unacceptable. The operator or the like operates the input device 60 to input a reason for unacceptability of the medical image. The CPU 111 acquires information indicating the acceptability or unacceptability determination of the medical image by the operator or the like or the reason for unacceptability as the inspection result of the medical image. In step S3, the CPU 111 performs the inference on the medical image acquired in step S1. Here, the CPU 111 performs the processing of acquiring the inspection result in step S2 and the processing of inference in step S3 in parallel.

Subsequently, in step S4, the CPU 111 determines whether the inspection result acquired in step S2 is acceptable. When the inspection result is acceptable (Y in S4), the CPU 111 causes the processing to proceed to step S7. When the inspection result is unacceptable (N in S4), the CPU 111 causes the processing to proceed to step S5. In step S5, the CPU 111 determines whether the inference on the medical image acquired in step S1 is being performed. When the inference is being performed (Y in S5), the CPU 111 causes the processing to proceed to step S6. When the inference is not being performed (N in S5), the CPU 111 causes the processing to proceed to step S7. In step S6, the CPU 111 stops the inference which is being performed and causes the processing to proceed to step S7.

Figure 4:
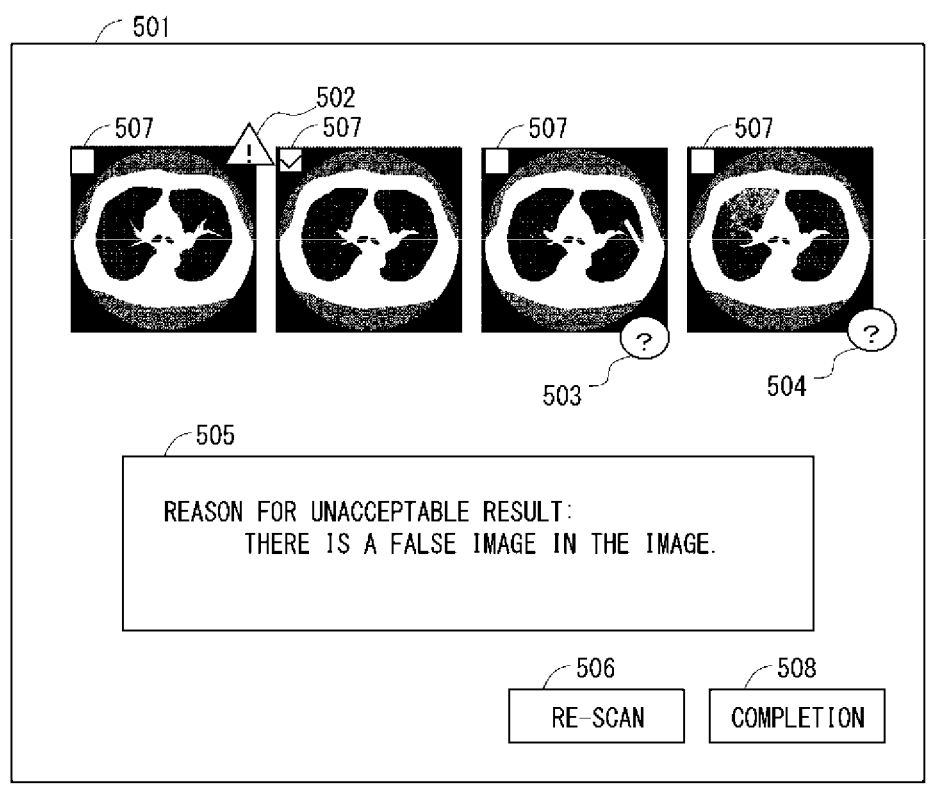
FIG. 4 is a diagram illustrating a display example of medical images according to the first embodiment.

In step S7, the CPU 111 displays the medical image of which the inspection result and/or the inference result can be obtained on the monitor 50. FIG. 4 illustrates a display example of medical images on the monitor 50. In the display example of FIG. 4, on the monitor 50, four medical images are displayed on a checking screen 501 of the medical images. In the medical image, an index 502 indicating that urgency is relatively high is also displayed, for example, when an inference result indicating that a disease risk is high is obtained. In the medical image, indexes 503 and 504 indicating that the inspection result acquired in step S2 is unacceptable are also displayed. When the operator or the like operates the input device 60 to press one index, information indicating content of the index is displayed on a detailed information display area 505. The content of the index displayed on the detailed information display area 505 is a comment which is input by the operator or the like in step S2 and shows the reason for unacceptability of the inspection result.

In the embodiment, the inference result of the medical image of which the inspection result is acceptable is displayed and the inference result of the medical image of which the inspection result is unacceptable is not displayed. Accordingly, in the display example of FIG. 4, an index such as the index 502 indicating the inference result is not displayed in the medical images in which the indexes 503 and 504 indicating that the inspection result is unacceptable are displayed. Thus, the operator or the like can check the inference result of the target medical image of which an appropriate inspection result is obtained.

The display example of FIG. 4 shows that the operator or the like presses the index 503 and a message indicating that there is a false image in the medical image (the inspection result is unacceptable) is displayed in the detailed information display area 505. In FIG. 4, the medical image in which the index 504 is displayed is a medical image in which halation occurs in part. Therefore, when the index 504 is pressed, information indicating that the halation occurs in the medical image is displayed as a reason why the inspection result is unacceptable in the detailed information display area 505. A re-scan button 506 for requesting re-scan is displayed on the monitor 50. The operator or the like can request the re-scan by pressing the re-scan button 506 as necessary while checking the information displayed in the detailed information display area 505 by pressing each index.

A check box 507 corresponding to each medical image is displayed on the monitor 50. The operator or the like can determine whether to transmit the medical image to the PACS 30 by switching between the check box 507 on and off. A completion button 508 used to complete the checking of the medical image displayed on the checking screen 501 is displayed on the monitor 50. When the operator or the like presses the completion button 508 after performing a necessary operation of checking the medical image displayed on the monitor 50 or requesting the re-scan, the medical image for which the check box 507 is turned on is transmitted to the PACS 30.

In step S8, based on whether the re-scan button 506 is pressed for the medical image displayed in step S7, the CPU 111 determines whether the re-scan of the medical image is requested. When the re-scan button 506 is pressed (Y in S8), the processing returns to step S1 and the CPU 111 re-acquires the medical image which is a re-scan target. Then, the CPU 111 acquires the re-scanned medical image and repeats the foregoing processing on the re-scanned medical image. Conversely, when the re-scan button 506 is not pressed for the medical image displayed in step S7 (N in S8), the processing proceeds to step S9.

In step S9, based on whether the completion button 508 is pressed, the CPU 111 determines whether the checking of the medical image displayed in step S7 is completed. When the completion button 508 is pressed (Y in S9), the CPU 111 causes the processing to proceed to step S10. Conversely, when the completion button 508 is not pressed (N in S9), the CPU 111 returns the processing to step S8. In step S10, the CPU 111 transmits the medical image for which the check box 507 is turned on among the medical images displayed on the monitor 50 to the PACS 30. Then, the CPU 111 ends the processing of the flowchart.

As described above, in the console 100 according to the embodiment, the acquisition and the inference of the inspection result of the medical image of the subject imaged on the gantry 10 are performed in parallel and the inference is controlled based on the inspection result. Thus, because the inference result based on the medical image of which the inspection result is acceptable is supplied, it is possible to further improve reliability of the inference result based on the medical image. Because the acquisition and the inference of the inspection result in the console 100 are performed in parallel, it is possible to further shorten a time from the completion of the imaging of the medical image to the completion of the inspection and the inference. When the inspection result is unacceptable, the inference which is being performed on the unacceptable medical image is stopped. Therefore, the unnecessary inference can be omitted. Accordingly, according to the embodiment, when an aortic dissection occurs in the subject, the inference result based on the appropriate inspection result can be obtained through the foregoing processing by the console 100, and thus it is possible to expect diagnosis of the subject more quickly than in the related art.

Second Embodiment

Next, a second embodiment will be described. In the following description, the same reference numerals are given to similar configurations to those of the first embodiment and detailed description thereof will be omitted. In the console 100 according to the second embodiment, a medical image of a subject imaged on the gantry 10 is generated, the generated medical image is reasoned, and subsequently an inspection result is acquired. Then, the control unit 102 of the console 100 controls output of an inference result to an external device based on the inspection result. While a target disease of the acquisition and the inference of the inspection result in the first embodiment is an aortic dissection, a target disease of the acquisition and the inference of the inspection result in the second embodiment is pneumothorax.

In the embodiment, with regard to the inference unit 104, a learned model in which a medical image including a pneumothorax part is learned as a target is generated in advance by machine learning using a known deep network such as a convolutional neural network (CNN). The inference unit 104 performs inference on the medical image using the generated model to detect a region of the pneumothorax in a medical image or draw a local region. The inference content is not limited thereto and a probability or the like at which the pneumothorax is included in the medical image may be calculated by the inference, as in the first embodiment.

In the second embodiment, the image processing unit 101 acquires tomographic data of a subject imaged on the gantry 10 from the data collection circuit 15 and generates a medical image based on the acquired data. The inference unit 104 performs inference on the medical image acquired by the image processing unit 101. Then, after the inference unit 104 completes the inference, the inspection result acquisition unit 103 acquires an inspection result of the medical image by the operator. The control unit 102 acquires the medical image from the image processing unit 101. The control unit 102 may acquire the medical image from the inference unit 104. The control unit 102 displays the inspection result acquired by the inspection result acquisition unit 103 and the medical image based on the inference result by the inference unit 104. The control unit 102 transmits the medical image selected by the operator or the like from the output unit 105 to the PACS 30.

Processing Flow

Figure 5:
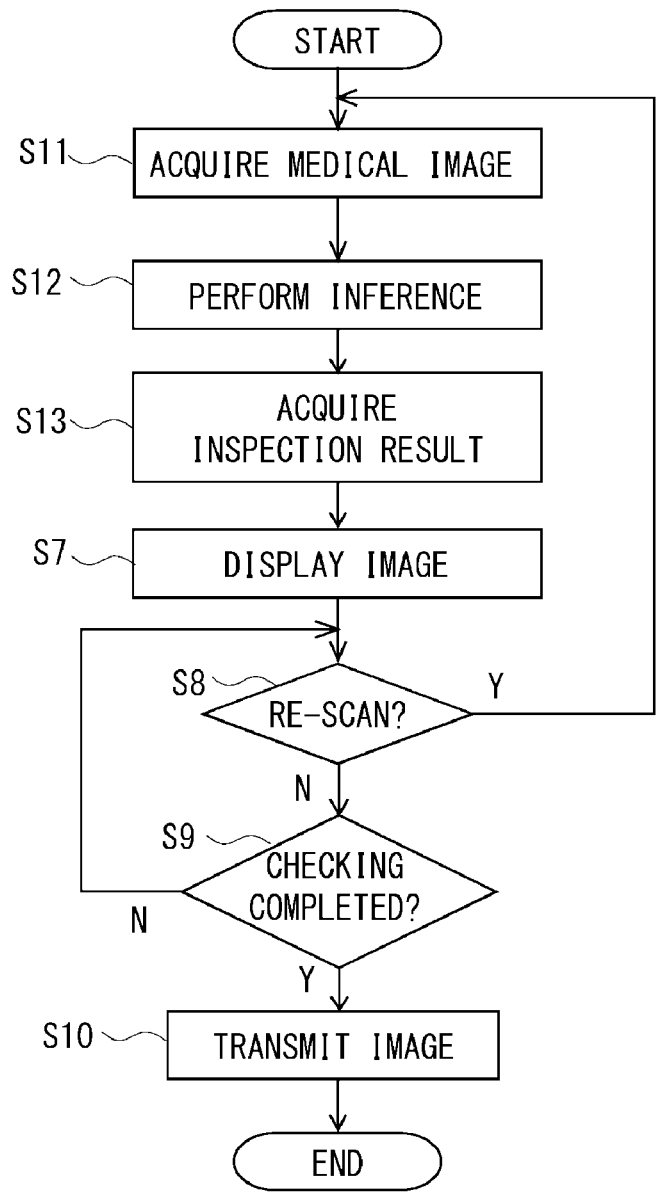
FIG. 5 is a flowchart illustrating processing performed according to a second embodiment.

Next, processing performed by the CPU 111 of the console 100 in the embodiment will be described with reference to the flowchart of FIG. 5. In the embodiment, the CPU 111 performs the inference on the medical image of the subject imaged on the gantry 10, subsequently acquires the inspection result, and displays the inference result for the operator or the like based on the acquired inspection result.

In step S11, the CPU 111 generates the medical image of the subject based on the data received from the data collection circuit 15 of the gantry 10. Thus, the CPU 111 acquires the medical image of the subject. Subsequently, in step S12, the CPU 111 performs the inference on the medical image acquired in step S11. After the inference in step S12 is completed, in step S13, the CPU 111 displays the medical image acquired in step S11 on the monitor 50 in response to an operation on the input device 60 by the operator or the like. The operator or the like inspects the medical image displayed on the monitor 50. Then, the operator or the like uses the acceptable button or the unacceptable button displayed on the monitor 50 to determine whether the medical image is acceptable or unacceptable. The operator or the like uses the input device 60 to input a reason for unacceptability of the medical image. The CPU 111 acquires information indicating the acceptability or unacceptability determination of the medical image by the operator or the like or the reason for unacceptability as the inspection result of the medical image.

When the processing of step S13 is completed, the CPU 111 causes the processing to proceed to step S7. The processing of steps S7 to S10 of the flowchart is the same as that of the first embodiment. Thus, as exemplified in FIG. 4, the medical image is displayed on the monitor 50. Then, the operator or the like can transmit the medical image for which the check box 507 is turned on to the PACS 30 by checking each medical image, performing a necessary operation such as re-scan, and subsequently pressing the completion button 508.

As described above, in the console 100 according to the embodiment, after the medical image of the subject imaged on the gantry 10 is reasoned, the inspection is performed and whether the inference result is output is determined based on the inspection result. Thus, only when the inspection result is acceptable, the inference result is output. Therefore, the appropriate inference result based on the inspection is supplied. For example, when the inference is completed in a shorter time than in the inspection on the medical image, the inference result is output based on the inspection result as soon as the inspection is completed by first completing the inference. As a result, it is possible to shorten a time from the completion of the imaging of the medical image to the completion of the inspection and the inference. Accordingly, according to the embodiment, when a pneumothorax disease occurs in the subject, the inference result based on the appropriate inspection result can be obtained through the foregoing processing by the console 100, and thus it is possible to expect diagnosis of the subject more quickly than in the related art.

The description of each embodiment is exemplary for describing the technology of the present disclosure and the technology of the present disclosure can be appropriately changed or combined within the scope of the gist of the present invention. For example, in the foregoing embodiments, the image processing unit 101, the control unit 102, the inspection result acquisition unit 103, the inference unit 104, and the output unit 105 of the console 100 may be realized by arithmetic circuits. Further, at least one of these processing units may be a dedicatedly designed workstation. The configurations of the arithmetic circuits of the processing units may be configured by different hardware. The configuration of at least some of the arithmetic circuits of the processing units may be configured by single hardware. That is, these processing units of the console 100 may be configured as arithmetic circuits such as a processor such as a CPU or a GPU and field programmable gate array (FPGA) chips. Further, these processing units may be configured by not only a single processor or arithmetic circuit but also a plurality of processors or arithmetic circuits.

In the foregoing embodiments, it is assumed that the operator or the like inspects the medical image acquired by the image processing unit 101, but the medical image may be inspected by the console 100. In this case, the CPU 111 performs inspection on the medical image acquired in steps S1 and S11 and processing of acquiring the inspection result instead of the foregoing processing of steps S2 and S13.

The inspection on the medical image may be performed for a single medical image or may be performed collectively on a plurality of medical images. Here, the inspection on a plurality of medical images may be performed collectively in units of patients, that is, each patient. When a plurality of kinds of inspection are performed for one patient, the inspection on a plurality of medical images may be performed in units of inspections. When a so-called imaging sequence in which a plurality of parts are imaged in a series of orders in the inspection, the inspection of the plurality of medical images may be performed collectively in units of imaging sequences. The inspection of a plurality of medical images may be performed collectively in units of volume data of imaging target parts, that is, a so-called imaging volume.

Figure 6:
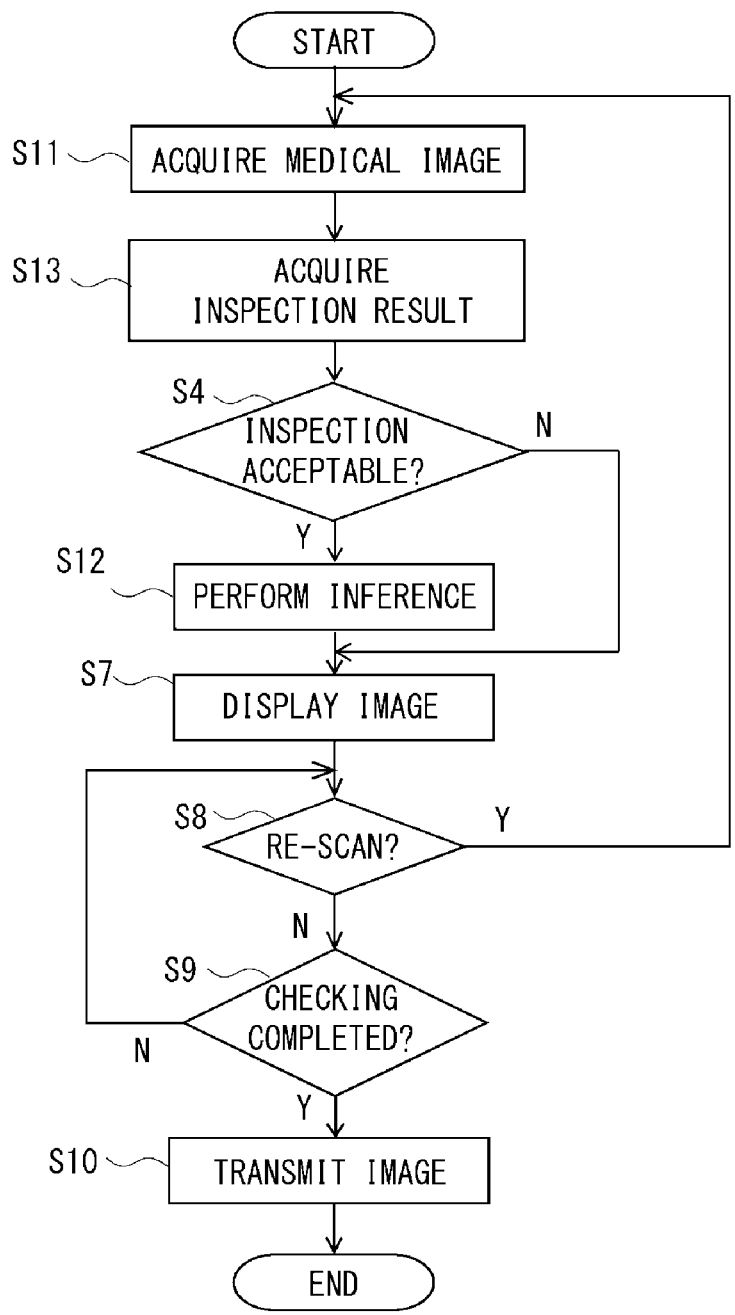
FIG. 6 is a flowchart illustrating processing performed according to a modification example.

In the second embodiment, the CPU 111 acquires the inspection result after the inference of the medical image is completed. However, as a modification example, the CPU 111 may perform the inference after the inspection result of the medical image is acquired. FIG. 6 is a flowchart illustrating processing performed by the CPU 111 in the modification example. As illustrated in the flowchart of FIG. 6, the CPU 111 acquires the medical image in the processing of step S11 and subsequently acquires the inspection result in the processing of step S13. The CPU 111 completes the processing of acquiring the inspection result in step S13 and subsequently performs the determination processing of step S4. Then, when the inspection result is acceptable in step S4 (Y in S4), the CPU 111 causes the processing to proceed to step S12. When the inspection result is unacceptable (N in S4), the CPU 111 causes the processing to proceed to step S7. Since the processing of steps S7 to S10 are the same as the above processing, detailed description will be omitted. In the modification example, the CPU 111 determines whether it is necessary to perform the inference at a stage when the inspection result is acquired. Thus, by not performing unnecessary inference when the inspection result is unacceptable, it is possible to expect to display the medical images or request the operator or the like to perform re-scan in a shorter time.

In the foregoing embodiment, processing may be performed to prompt a doctor or the like to interpret a medical image indicating that an inference result is abnormal prior to a medical image indicating that an inference result is normal. For example, the CPU 111 transmits information indicating the medical image which is first interpreted along with the medical image and the inference result to the PACS 30. In this case, a priority may be set in accordance with urgency of the inference result. The priority may be set in the console 100 by the operator or the like or the priority in accordance with the urgency of the inference result may be set in advance in the console 100.

In the foregoing embodiments, the medical images of the subject imaged in the tomographic apparatus 1 have been assumed to be the inspection and inference targets. Here, the present invention is not limited to the modality apparatus that captures the medical images in each embodiment. For example, instead of the tomographic apparatus 1, an MRI apparatus, an ultrasonic diagnostic apparatus, an X-ray mammographic apparatus, or the like may be used. Accordingly, the technology of the present disclosure can be applied to various tomographic apparatuses radiating waves with a predetermined wavelength such as an ultrasonic waves or electromagnetic waves such as X rays to a subject. Further, a target disease which is aortic dissection has been assumed in the first embodiment and a target disease which is pneumothorax has been assumed in the second embodiment. However, the target disease is not limited thereto and may be a malignant neoplasm (a malignant tumor or a cancer) or other diseases.

In the foregoing embodiments, the inference result may be added to a tag which is supplementary information for identifying data elements of digital imaging and communications in medicine (DICOM). When the inference result shows that the medical image includes a part which may require treatment, information indicating the inference result may be added to an electronic medical chart.

In the foregoing embodiment, a case is assumed in which, when the inspection result of the medical image is restricted to a part corresponding to an imaged part specified from an imaging order despite being unacceptable, the inspection result is acceptable. Accordingly, when the imaged part is identified based on information regarding the imaging order and an inspection result of the part is acceptable, the console 100 may be configured to output the inference result obtained through the foregoing processing.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the technology of the present disclosure, it is possible to perform inference on medical images based on an appropriate inspection result.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-158315, filed on Aug. 30, 2019, which is hereby incorporated by reference herein in its entirety.

What is claimed is:

1. An information processing apparatus comprising:
a processor; and
a memory storing a program which, when executed by the processor, causes the information processing apparatus to:
acquire a medical image obtained by imaging a subject;
acquire an inspection result of the medical image;
perform inference on the medical image; and
control outputting of an inference result of the medical image to an external device based on the inspection result of the medical image, wherein the program causes the information processing apparatus to acquire the inspection result of the medical image and perform the inference on the medical image in parallel, and wherein an inspection of the medical image is performed on a part corresponding to an imaged part of the subject specified from an imaging order, and in the case where the inference on the medical image is completed earlier than the acquisition of the inspection result of the medical image on the part corresponding to the imaged part of the subject, the program causes the information processing apparatus not to output the inference result of the medical image to the external device until the inspection result of the medical image on the part corresponding to the imaged part of the subject is acceptable.

2. The information processing apparatus according to claim 1, wherein the program further causes the information processing apparatus to not output the inference result of the medical image to the external device when the inspection result is unacceptable.

3. The information processing apparatus according to claim 1, wherein the program further causes the information processing apparatus to:
acquire, when the inspection result is unacceptable, a medical image of the subject by re-scan and acquire an inspection result of the medical image of the subject by the re-scan,
perform inference on the medical image of the subject by the re-scan, and
output an inference result of the inference on the medical image of the subject by the re-scan to the external device when the inspection result of the medical image of the subject by the re-scan is acceptable.

4. The information processing apparatus according to claim 1, wherein the program further causes the information processing apparatus to perform the inference using a model generated by machine learning using medical images.

5. An information processing method comprising the steps of:
acquiring, by a first acquisition mechanism, a medical image obtained by imaging a subject;
acquiring, by a second acquisition mechanism, an inspection result of the medical image;
performing, by an inference mechanism, inference on the medical image; and
controlling, by a control mechanism, outputting of an inference result of the medical image by the inference mechanism to an external device based on an inspection result of the medical image acquired by the second acquisition mechanism,
wherein acquiring the inspection result of the medical image and performing the inference on the medical image are performed in parallel, and
wherein an inspection of the medical image is performed on a part corresponding to an imaged part of the subject specified from an imaging order, and in the case where the inference on the medical image is completed earlier than the acquisition of the inspection result of the medical image on the part corresponding to the imaged part of the subject, the inference result of the medical image is not output to the external device until the inspection result of the medical image on the part corresponding to the imaged part of the subject is acceptable.

6. The information processing method according to claim 5, wherein the control mechanism does not output the inference result of the medical image to the external device when the inspection result is unacceptable.

7. The information processing method according to claim 5, further comprising the steps of:
acquiring, by the first acquisition mechanism, a medical image of the subject by re-scan and acquiring, by the second acquisition mechanism, an inspection result of the medical image of the subject by the re-scan when the inspection result is unacceptable;
performing, by the inference mechanism, inference on the medical image of the subject by the re-scan, and
outputting, by the control mechanism, an inference result of the inference on the medical image of the subject by the re-scan to the external device when the inspection result of the medical image of the subject by the re-scan is acceptable.

8. The information processing method according to claim 5, wherein the inference mechanism performs the inference using a model generated by machine learning using medical images.

9. A non-transitory computer-readable storage medium that stores a program causing a computer to execute the steps of:
acquiring, by a first acquisition mechanism, a medical image obtained by imaging a subject;
acquiring, by a second acquisition mechanism, an inspection result of the medical image;
performing, by an inference mechanism, inference on the medical image; and
controlling, by a control mechanism, outputting of an inference result of the medical image by the inference mechanism to an external device based on an inspection result of the medical image acquired by the second acquisition mechanism,
wherein the program causes the information processing apparatus to acquire the inspection result of the medical image and perform the inference on the medical image in parallel, and
wherein an inspection of the medical image is performed on a part corresponding to an imaged part of the subject specified from an imaging order, and in the case where the inference on the medical image is completed earlier than the acquisition of the inspection result of the medical image on the part corresponding to the imaged part of the subject, the program causes the information processing apparatus not to output the inference result of the medical image to the external device until the inspection result of the medical image on the part corresponding to the imaged part of the subject is acceptable.

10. A tomographic apparatus comprising:
the information processing apparatus according to claim 1; and
a data collection unit configured to collect tomographic data of the subject,
wherein the program further causes the information processing apparatus to acquire the medical image based on the tomographic data.

11. An information processing apparatus comprising:
a processor; and
a memory storing a program which, when executed by the processor, causes the information processing apparatus to:
acquire a medical image obtained by imaging a subject;
acquire a first inspection result of the medical image;
perform inference on the medical image; and output an inference result of the medical image to an external device, wherein in the case where the first inspection result of the medical image is unacceptable and a second inspection result, acquired by the information processing apparatus, of a part corresponding to an imaged part of the subject specified from an imaging order is acceptable, the program causes the information processing apparatus to output the inference result of the medical image on the medical image to the external device.

12. An information processing method comprising the steps of:

acquiring, by a first acquisition mechanism, a medical image obtained by imaging a subject;

acquiring, by a second acquisition mechanism, an inspection result of the medical image;

performing, by an inference mechanism, inference on the medical image; and controlling, by a control mechanism, outputting of an inference result of the medical image by the inference mechanism to an external device based on an inspection result of the medical image acquired by the second acquisition mechanism, wherein, in the case where the first inspection result of the medical image is unacceptable and a second inspection result of a part corresponding to an imaged part of the subject specified from an imaging order is acceptable, the inference result of the medical image is not output to the external device.

* * * * *